United States Patent [19]

Badera et al.

[11] Patent Number: 5,040,543
[45] Date of Patent: Aug. 20, 1991

[54] MOVABLE CORE GUIDEWIRE

[75] Inventors: Michael J. Badera, Queensbury; Steven J. Denton, II, Corinth; Evan T. Lessick, Queensbury; Frederick F. Puliafico, Scotia, all of N.Y.

[73] Assignee: C. R. Bard, Inc., Murray Hill, N.J.

[21] Appl. No.: 557,596

[22] Filed: Jul. 25, 1990

[51] Int. Cl.$^5$ .............................................. A61B 5/00
[52] U.S. Cl. ..................................... 128/772; 128/657
[58] Field of Search ............... 128/657, 772, DIG. 14; 604/167, 170, 95, 96

[56] References Cited

U.S. PATENT DOCUMENTS

| | | | |
|---|---|---|---|
| 4,279,245 | 7/1981 | Takagi | 128/DIG. 14 |
| 4,548,206 | 10/1985 | Osborne | 128/772 |
| 4,579,127 | 4/1986 | Haacke | 128/772 |
| 4,676,249 | 6/1987 | Arenas | 128/772 |
| 4,713,070 | 12/1987 | Mano | 128/DIG. 14 |
| 4,719,924 | 1/1988 | Crittenden | 128/657 |
| 4,779,628 | 10/1988 | Machek | 128/772 |
| 4,808,164 | 2/1989 | Hess | 604/170 |
| 4,841,976 | 6/1989 | Packard | 128/772 |
| 4,895,168 | 1/1990 | Machek | 128/772 |
| 4,921,482 | 5/1990 | Hammerslag | 128/772 |
| 4,922,924 | 5/1990 | Gambale | 128/772 |

OTHER PUBLICATIONS

Cordis Corporation brochure entitled Emerald Guidewires.
Schneider (U.S.A.), Inc., A Pfizer Company brochure entitled Begin With Schneider Guidewires.

*Primary Examiner*—William E. Kamm
*Assistant Examiner*—Robert L. Nasser, Jr.
*Attorney, Agent, or Firm*—Wolf, Greenfield & Sacks

[57] ABSTRACT

A movable core guidewire for use in guiding a catheter to an internal body location includes an elongate, flexible helical coil having a lumen extending longitudinally therethrough for receiving a movable core wire. The movable core wire has a flexible polymeric element extending from the distal end which facilitates smooth movement of the movable core wire within the lumen of the helical coil. The use of this polymeric element provides a movable core guidewire that has a better feel for the physician when the movable core is slid longitudinally through the lumen of the helical coil and by reducing the force necessary to push or pull the core wire through the lumen of the helical coil and also reduces the risk of the core wire striking through the helical coil.

26 Claims, 4 Drawing Sheets

MOVABLE CORE GUIDEWIRE

FIELD OF THE INVENTION

This invention relates to guidewires used with catheters, for example, to guide and place a catheter in a blood vessel.

BACKGROUND OF THE INVENTION

This invention relates to guidewires commonly used in the placement of catheters at various locations in a patient's body, such as in the cardiovascular system, e.g., balloon catheters and angiographic catheters. Such catheters may be too flexible to be advanced unsupported through the patient's vasculature and require a quidewire to support and guide the catheter into place.

Typically, a guidewire first is manipulated through the patient's vasculature to a desired location. The catheter, which has a lumen adapted to receive the guidewire, then is advanced over the guidewire to follow it to the desired location. One very common quidewire construction has an elongate, flexible helical coil having a proximal end and a distal end, the latter being inserted into the patient. An internal core wire typically extends through the coil, the proximal end of the core wire being attached to the proximal end of the coil. The internal core wire may be tapered at its distal end or may not extend fully to the distal end of the helical coil thus providing a segment of increased flexibility at the distal end of the guidewire. The more flexible distal segment is advantageous in that it is less likely to cause trauma to a blood vessel. Guidewires also commonly have a safety wire which extend within the coil from the proximal to the distal end. The safety wire prevents detachment of a segment of the coil, should such a segment break off within the body. In some guidewires used for cardiovascular purposes, the distal portion of the helical coil is J shaped to provide improved steerability of the guidewire into various branches of a blood vessel.

This invention in particular relates to a class of guidewires having an inner core wire that is movable longitudinally within the lumen of the helical coil. The movable core wire permits variability in the flexibility of the distal end of the guidewire. The core wire can be drawn proximally to provide increased flexibility in the distal end or can be advanced towards the distal end of the helical coil to increase the stiffness at the distal end. Variable flexibility enables the guidewire to be used in situations where it is important to be able to vary the tip configuration from a soft, flexible atraumatic configuration to a stiffer, more easily pushed configuration.

Movable core guidewires having a helical coil with a J shaped distal portion are sometimes used for cardiovascular applications. The movable core is advantageous over the fixed core for the J-shaped guidewires because the size of the curve on the distal portion can be adjusted by moving the core wire distally (to straighten out the J) or moving the core wire proximally (to reform the J). The ability to control the shape of the J-tip increases the facility by which the guidewire can be manipulated to select a desired blood vessel at branch points.

It is very important, for patient safety, that the distal tip of the movable core does not strike through the side of the guidewire through a pair of adjacent turns of the helical coil. The risk of such "strike through" is somewhat greater when the distal portion of the guidewire is disposed in a more sharply curved or tortuous blood vessel or body lumen. Additionally, when the guidewire is advanced into such difficult vasculature, it increases the frictional forces developed between the movable core tip and the inner surface of the helical coil thus making it more difficult to move the movable core wire through the helical coil and also reducing the physician's sensitivity to the feel of the movable core. It is among the general objects of the invention to provide an improved movable core guidewire which avoids the foregoing difficulties.

SUMMARY OF THE INVENTION

The movable core guidewire of the present invention includes an elongate, flexible helical coil having a lumen extending longitudinally therethrough for receiving a movable core wire. The movable core wire has a flexible polymeric element extending from the distal end of the movable core wire which facilitates smooth movement of the movable core wire within the lumen of the helical coil and also reduces the risk of the core wire striking through the helical coil. The polymeric element is made of a lubricious polymer such as polytetrafluoroethylene or tetrafluoroethylene which reduces the force necessary to push or pull the core wire through the lumen of the helical coil. The use of this polymeric element provides a movable core guidewire that has a better, more sensitive feel for the physician when the movable core is slid longitudinally through the lumen of the helical coil particularly when the distal end of the guide is in tortuous vasculature.

Accordingly, it is an object of the present invention to provide an improved movable core guidewire for guiding a catheter within a body blood vessel.

It is another object of the invention to provide a movable core guidewire which provides a better feel for the physician when moving the core wire.

Another object of the invention is to provide a movable core guidewire having an inner core which can be advanced through the lumen of a helical coil with reduced friction.

Another object of the invention is to provide a movable core guidewire which reduces the risk of the core wire striking through the helical coil outer casing.

Yet another object of the invention is to provide a movable core guidewire which is relatively uniform with regard to variability of the feel from one guidewire to the next.

DESCRIPTION OF THE DRAWINGS

The foregoing and other objects and advantages of the invention will be appreciated more fully from the following further description thereof with reference to the accompanying drawings wherein.

DESCRIPTION OF THE PREFERRED EMBODIMENT

Figure 1:
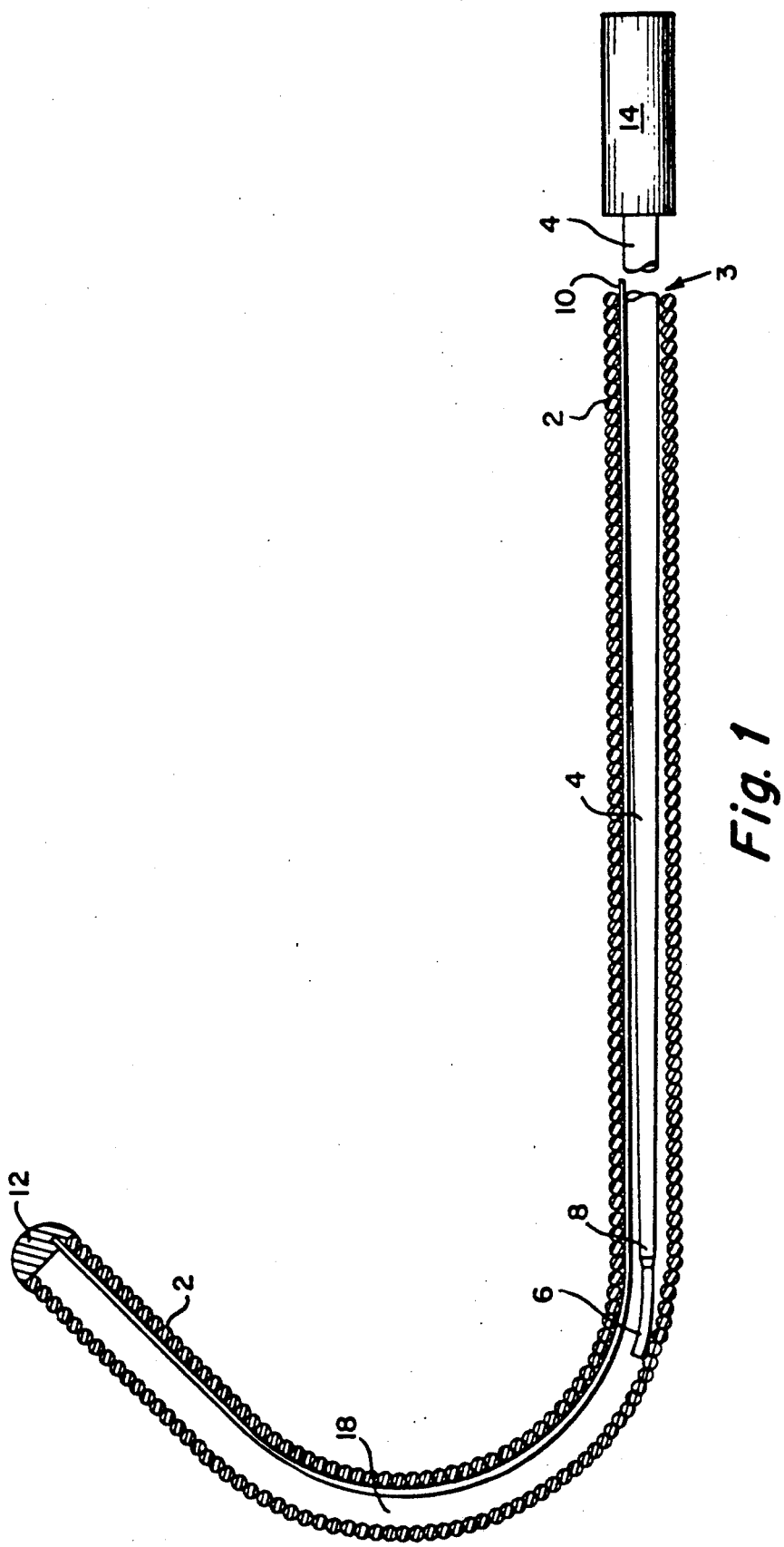
FIG. 1 is an enlarged sectional, fragmented illustration of the movable core guidewire of the present invention.

FIG. 1, illustrates the guidewire which may be considered as having a proximal end (to the right in FIG. 1) and a distal end (to the left in FIG. 1). The guidewire includes an elongate, flexible, helical coil which may be of any outer diameter, it being noted that the most common diameters for such guidewires are 0.035" or 0.038". The guidewire necessarily will be longer than the catheter with which it is intended to be used so that it may be manipulated from its proximal end while the distal end projects beyond the distal end of the catheter. Guidewires incorporating the present invention may be made in a wide variety of lengths corresponding to the lengths of the catheters with which they are intended to be used. By way of example only, the length of the guidewire may be between 100–175 cm. The proximal end of the helical coil is open, as indicated at 3, several of the most proximal turns of the helical coil 2 being joined together, as by soldering or resistance welding. The distal end of the coil is closed, as by a tip weld or soldered end indicated at 12. The tip weld 12 is hemispherical and smooth to further facilitate smooth movement of the guidewire within the body and reduce potential trauma to the body caused by the insertion of the guidewire. A movable core wire 4 is slidably received within the lumen of the helical coil 2. The movable core wire 4 has a polymeric element 6 on its distal end 8. The guidewire also preferably includes a slender safety wire 10 extending longitudinally through the coil. The safety wire 10 is attached to the proximal end of the coil at the joint and at the tip joint 12 distal end of the helical coil 2. The safety wire 10 may be coated with a lubricious material, such as Teflon (polytetrafluoroethylene and tetrafluoroethylene).

The helical coil 2 can be wound from round or other cross section (preferably round) stainless steel wire 0.007" diameter. The helical coil preferably is coated with a lubricious polymer such as Teflon to facilitate smooth movement of the guidewire within the lumen of the catheter with which it is to be used as well as within the lumen of the blood vessel or other body organ. The coating preferably is applied to the helical coil after the wire is already wound so that only the outer surface of the wire which is going to contact the inner surface of the catheter lumen or body organ is so coated. The outside diameter of the helical coil 2 will vary depending upon the inside diameter of the catheter which it is going to guide. The size of the catheter is selected depending upon factors such as the size and location of the organ or blood vessel which is going to be catheterized.

The movable core wire 4 is slidably received within the lumen of the helical coil 2. The core wire 4 preferably is formed from stainless steel and preferably is coated with a lubricious polymer to aid in the smooth movement of the movable core wire 4 within the lumen of the helical coil 2. Examples of such polymers include polytetrafluoroethylene and tetrafluoroethylene, e.g. Teflon. The coating is quite thin, of the order of 0.0002" thickness and may be defined by application of a thin primer coat of Teflon, omitting the usually thicker second enamel coating of the Teflon coating process. The movable core wire 4 can be coated over its entire length from the proximal to the distal end or it can be coated over a portion of its length. A distal segment of the core wire may be uncoated, in the region where the core wire is ground down to a taper, as described more fully below. Additionally, the proximal end of the core wire also may remain uncoated to facilitate attachment of a handle. The portion of the length of the movable core wire 4 that is coated with the polymer should be that which is necessary or sufficient to provide smooth movement of the core wire within the lumen of the helical coil 2. The distal-most segment of the tapered region will be covered by a lubricious polymeric material extending over a length of about 1 to 3 cm. The diameter of the movable core wire 4 varies depending upon the inside diameter of the helical coil 2. For example, for a 0.035" or 0.038" guidewire formed from 0.007" diameter wire, the guidewire will have an inner lumen diameter of 0.021" or 0.024", the movable core wire preferably has a diameter of 0.016" or 0.018". It should be understood, however, that these dimensions are illustrative only and that they may be modified, particularly if other materials are used for any of the helical coil, movable core wire or safety wire.

The proximal end 16 of the core wire 4 preferably has a handle 14 which can be formed from the same material as the helical coil or can be formed from a plastic.

The distal portion 8 of the core wire 4 may be tapered. The taper may be a step taper or a gradual continuous taper. The tapered portion preferably extends over a distance of about 4 cm but may be between 1 to 3 cm. In the step taper, the diameter of the distal portion 8 of the core wire is reduced in progressive distinct increments alternating short tapered segments with somewhat longer continuous diameter barrel segments. In the continuous taper configuration, the taper is continuous over the distal portion 8. By way of example, the core wire may taper down to a diameter at its distal tip of the order of 0.010".

Figure 2:
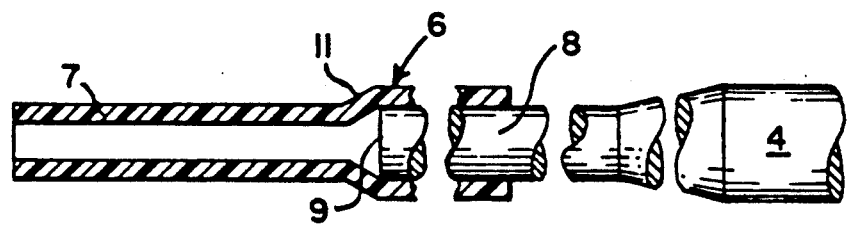
FIG. 2A through 2C are enlarged fragmented illustrations of the distal region of embodiments of the movable core wire of the guidewire having a polymeric element attached to and extending distally from the distal end of the core wire.
Figure 2A:
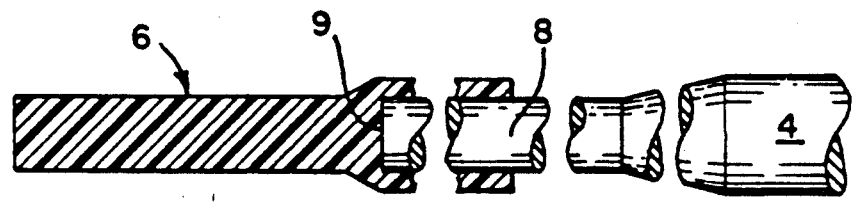
Figure 2B:
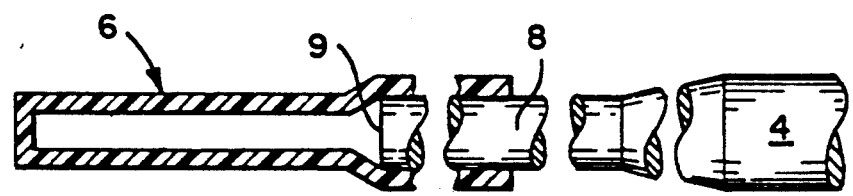

In accordance with the invention and as shown in FIG. 2A through 2C, a flexible, elongate polymeric element 6 is attached to and extends distally from the distal end 8 of the movable core wire 4. The polymeric element 6 can be applied to the core wire 4 using conventional manufacturing technologies such as shrink tubing, injection molding, or dipping. Preferably, the polymeric element 6 is formed from a length of shrinkable tubing and applied to the core wire 4 by using shrink tubing techniques. The polymeric element 6 can be hollow or solid and also can be open ended or close ended. The preferred polymeric element 6 is hollow and open ended which provides a greater flexibility than a solid polymeric element 6. The polymer for element 6 should be based on such factors as its flexibility, degree of lubricity and the ease of applying the polymer onto the core wire 4. Examples of lubricious polymers which can be used in this invention include polytetrafluoroethylene or tetrafluoroethylene, e.g. Teflon.

The polymeric element 6 preferably is formed from a tubular sleeve of heat shrinkable polymeric material selected so that it may be placed over the distal end of the core wire and then heat shrunk tightly about the core wire with a distal segment of the sleeve defining the flexible tip segment 7 that extends distally beyond the distal tip of the core wire. The tip segment 7 is of cylindrical shape and preferably narrows down to a smaller diameter than the portion of the sleeve 6 that is mounted on the distal tip of the core wire. For example, in a core wire in which the distal tip 9 of the core wire is 0.010" in diameter, the diameter of the portion of the sleeve that is disposed on the core wire may be of the order of 0.016". The distal tip element preferably necks down (indicated at 11) to a smaller diameter, preferably of the order of an inner diameter of 0.008" and an outer diameter of about 0.014". The tip extension may be of the order of 0.5 mm to about 1 mm (0.020" to about 0.040"). The wall thickness of the sleeve is about 0.003". Although the specific starting tube from which the foregoing configuration is made may vary, depending on the specific material used, we have found that a heat shrinkable Teflon tube having an inner diameter of about 0.020" and a wall thickness of about 0.003" results in satisfactory tip element. It may be noted that the necking down to a slightly smaller diameter of the tip extension tends to result in a weaker cross-section for the tip extension 7 and facilitates its bending in a manner contemplated by the present invention.

Figure 4:
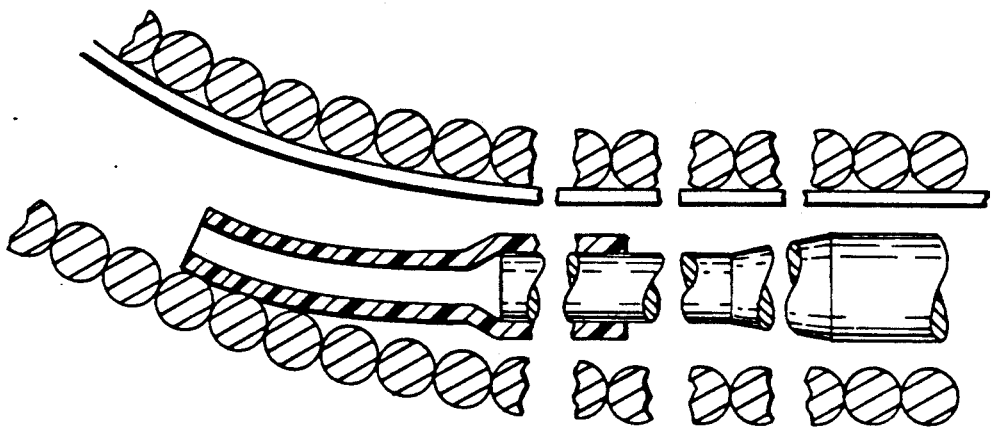
FIG. 4 depicts one manner in which the tip element may prevent the core wire from protruding through the helical coil.
Figure 5:
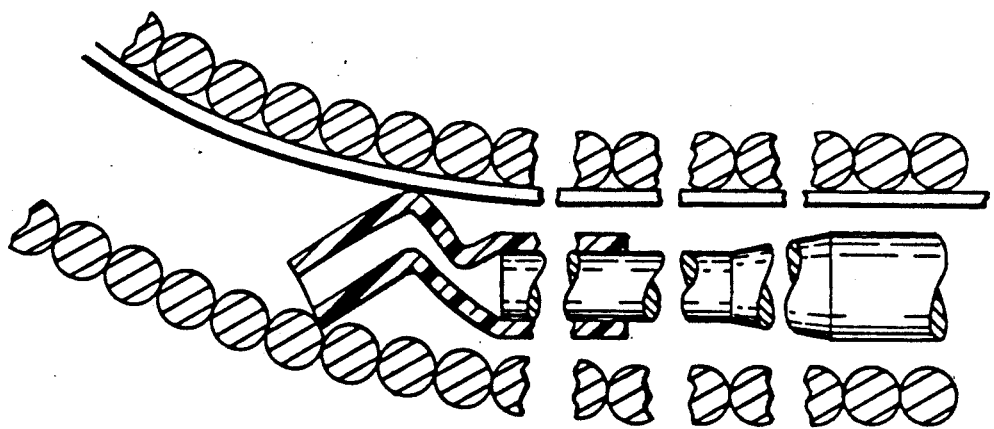
FIG. 5 illustrates another manner in which the tip element may function to prevent the core wire from striking through the coil.

The polymeric element 6 facilitates smooth movement of the movable core wire 4 within the lumen of the helical coil 2 and also prevents the movable core wire 4 from striking through the coils of the wound helical coil 2 into the body lumen such as a blood vessel. Such protrusion of the movable core wire 4 could cause considerable trauma to a blood vessel. The polymeric element 6 prevents protrusion of the core wire 4 through the helical coil 2 by bending or folding as shown in FIGS. 1 and 4 or collapsing in somewhat of an accordian-like fashion as shown in FIG. 5. In the mode of operation suggested in FIG. 4, the tip extension 7 of the polymeric element 6 bends toward the inside of the lumen of the coil 2 and thereby continually directs the distal end 8 of the movable core wire through the lumen. Should the tip extension of the polymeric element 6 become caught on a turn of the helical coil, the highly flexible nature of the tip extension 7 will cause it to collapse, as suggested somewhat diagrammatically in FIG. 5. The collapsed tip portion 7 will assume somewhat enlarged dimensions such that it cannot pass through a pair of adjacent turns of the helical coil and will tend to be deflected back into the lumen of the coil.

The polymeric element 6 also facilitates smooth movement of the core wire particularly in the distal region of the guidewire. It is the distal region of the guidewire that likely will encounter sharply curved or tortuous body lumens and will present maximum resistance to movement of the movable core. By forming the polymeric element from a lubricious material, as well as by coating a segment of the core wire proximally of the polymeric element 6 with a lubricious material, the frictional forces developed between the core wire and the coil will be reduced, even when the distal portion of the coil is in a sharply curved or tortuous configuration.

Figure 3A:
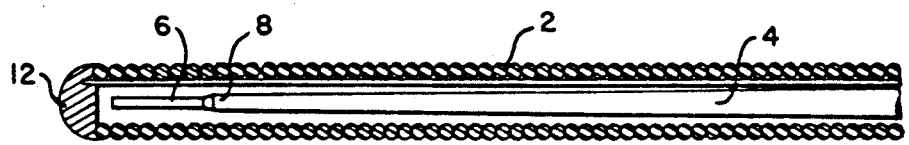
FIGS. 3A through 3C are enlarged diagrammatic illustrations showing the manner in which the movable core wire can be manipulated to vary the degree of curvature at the distal end of a guidewire having a J-tip.
Figure 3B:
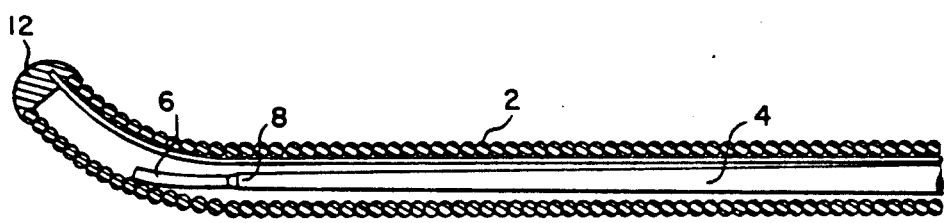
Figure 3C:
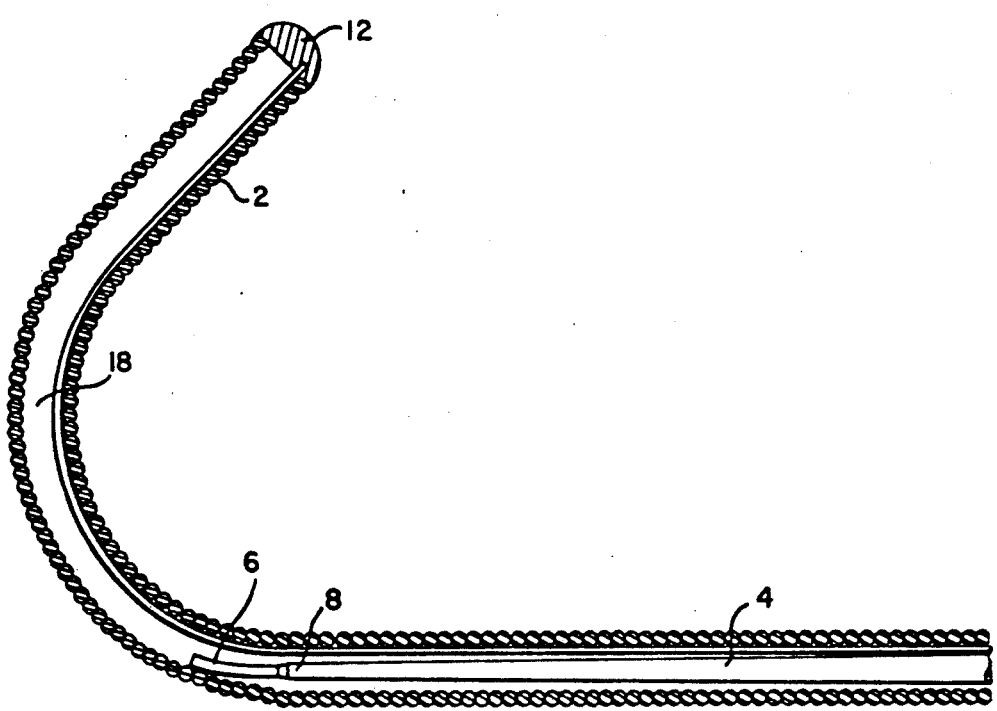

Smooth movement of the core wire 4 within the lumen of the helical coil 2 also is important when the distal portion of the helical coil 2 is J-shaped as shown by FIGS. 3A–3C. These figures show the sequential mechanism of pushing the movable core wire 4 into the helical coil 2 towards the distal end of the helical coil 2 for purposes of straightening out the J-shaped distal portion (FIG. 3A) and pulling the movable core wire 4 towards the proximal end to reform the J-shaped distal portion (FIGS. 3B and 3C). When the movable core wire 4 approaches the J-shaped portion 18 of the helical coil 2 and begins to straighten out the J shaped portion, it requires less force to push a core wire 4 having a polymer element 6 on the tip than the same coated core wire 4 without the polymer element 6.

Thus, it will be appreciated that the invention provides an improved movable core type of guidewire in which the frictional drag developed between the movable core and the guidewire lumen is reduced, even in sharply curved and tortuous configurations and also where the risk of the tip of a movable core wire striking through the helical coil is reduced. Moreover, the foregoing advantages and objects are achieved with a very simple construction, with the device being relatively easy and inexpensive to fabricate.

It should be understood, however, that the foregoing description of the invention is intended merely to be illustrative thereof and other embodiments, modifications and equivalents may be apparent to those skilled in the art without departing from its spirit.

Having thus described the invention what I desire to claim and secure by Letters Patent is:

1. A movable core guidewire for guiding a catheter to a selected site within the body, comprising:
   an elongate, flexible helical coil having a proximal and distal end, said helical coil having a lumen extending longitudinally therethrough from the proximal to the distal end for slidably receiving a movable core wire; and
   a movable core wire having a proximal and distal end and a flexible, lubricious polymeric extension tip attached to and extending from the distal end of the core wire, the extension tip being adapted to flex and follow curved configurations of the coil thereby to guide the core wire through the curved portions of the coil to prevent the core wire from striking through the coil.

2. A movable core guidewire as claimed in claim 1 further comprising a safety wire extending longitudinally from the proximal to the distal end.

3. A movable core guidewire as claimed in claims 1 or 2 wherein the flexible polymer tip extension extends distally up to three millimeters beyond the distal tip of the movable core wire.

4. A movable core guidewire as defined in claims 1 or 2 wherein the flexible polymeric extension extends distally about 1 mm beyond the distal tip of the movable core wire.

5. A movable core guidewire as claimed in claims 1 or 2 wherein the polymeric tip extension is a hollow tubular member.

6. A movable core guidewire as defined in claim 5 wherein the polymeric element comprises a tube heat shrunk onto the distal end of the core wire, the tubular tip extension comprising the distal tip of the heat shrunk tube.

7. A movable core guidewire as defined in claim 6 wherein the tip extension is necked down to a smaller outer diameter than the portion of the polymeric element that is disposed on the distal tip of the core wire.

8. A movable core guidewire as defined in claim 5 wherein the polymeric extension is open-ended.

9. A movable core guidewire as claimed in claims 1 or 2 wherein the polymeric tip extension is a solid member.

10. A movable core guidewire as claimed in claim 9 wherein the end of the polymeric extension is close-ended.

11. A movable core guidewire as claimed in claims 1 or 2 wherein the distal portion of the movable core wire is tapered.

12. A movable core guidewire as claimed in claim 11 wherein the outside diameter of the polymeric extension narrows from the distal tip of the core wire to the distal tip of the extension.

13. A movable core guidewire as claimed in claim 2 further comprising a tip joint at the distal end of the helical coil.

14. A movable core guidewire as claimed in claim 2 wherein the movable core is coated with a lubricious polymer.

15. A movable core guidewire as claimed in claim 2 wherein the movable core is coated with a lubricious polymer over a substantial portion of its length.

16. A movable core guidewire as claimed in claim 2 wherein the polymeric element is made of a polymer selected from the group consisting of a polytetrafluoroethylene or tetrafluoroethylene.

17. A movable core guidewire as claimed in claim 2 wherein the polymeric extension is open-ended.

18. A movable core guidewire as defined in claim 17 wherein the polymeric element comprises a tube heat shrunk onto the distal tip of the core wire.

19. A movable core guidewire as defined in claim 18 wherein the tip extension is necked down to a smaller outer diameter than the portion of the polymeric element that is disposed on the distal tip of the core wire.

20. A movable core guidewire as claimed in claim 2 wherein the end of the polymeric extension is closed-ended.

21. A movable core guidewire for guiding a catheter to a selected site within the body comprising:
an elongate flexible helical coil having a proximal end and a distal end, the helical coil having a lumen extending longitudinally therethrough from the proximal to the distal end for slidably receiving a movable core wire;
a movable core wire having a proximal end and a distal end and being slidably received in the lumen of the helical coil, a distal portion of the core wire being tapered and terminating in a distal tip smaller in diameter than the more proximal portions of the core wire;
an elongate flexible tubular element formed from a flexible polymeric material mounted on the distal end of the tapered portion and having a tip extension extending distally beyond the distal tip of the core wire, the tip extension being dimensioned with respect to the core wire and helical coil such that when the tip extension engages the inner surface of the helical coil, the extension will deform in a manner that resists the tip of the core wire from protruding between a pair of adjacent coils.

22. A movable core guidewire as defined in claim 21 wherein the helical coil, guidewire and polymeric tip element are dimensioned to be in the following proportions:
said helical coil being formed from wire about 0.007" in diameter and being wound into a coil having an outer diameter of about 0.035" to about 0.038";
the core wire being formed from stainless steel and having a diameter along most of its length of approximately 0.016" to 0.018" and tapering, at its distal tip to a diameter of the order of 0.010";
the tubular element being between about 1 cm to 3 cm long and having a wall thickness of the order of 0.003", the distal tip of the extension being narrowed to about 0.008" in diameter, the length of the tip extension being between about 0.5 mm to about 2 mm.

23. A guidewire as defined in any of claims 1-15, 21 or 22 further comprising:
the helical coil having a preferred curved tip at its distal end.

24. A guidewire as defined in claim 23 further comprising the polymeric element including a proximal portion that extends over and covers a distal portion of the distal end of the core wire.

25. A guidewire as defined in any of claims 1-15, 21 or 22 further comprising:
the helical coil having a straight tip at its distal end.

26. A guidewire as defined in claim 25 further comprising the polymeric element including a proximal portion that extends over and covers a distal portion of the distal end of the core wire.

* * * * *